(12) United States Patent
Amirkhanian et al.

(10) Patent No.: US 6,828,567 B2
(45) Date of Patent: Dec. 7, 2004

(54) OPTICAL DETECTION IN A MULTI-CHANNEL BIO-SEPARATION SYSTEM

(75) Inventors: Varouj Amirkhanian, La Crescenta, CA (US); Ming-Sun Liu, Brea, CA (US)

(73) Assignee: Biocal Technology, Inc., Irvine, CA (US)

( * ) Notice: Subject to any disclaimer, the term of this patent is extended or adjusted under 35 U.S.C. 154(b) by 0 days.

(21) Appl. No.: 10/060,052

(22) Filed: Jan. 28, 2002

(65) Prior Publication Data

US 2002/0113213 A1 Aug. 22, 2002

Related U.S. Application Data

(60) Provisional application No. 60/264,553, filed on Jan. 26, 2001.

(51) Int. Cl.[7] .............................................. G01N 21/64
(52) U.S. Cl. .................................... 250/458.1; 356/344
(58) Field of Search .......................... 250/458.1, 459.1, 250/461.1, 461.2; 356/317, 318, 344, 417; 204/452

(56) References Cited

U.S. PATENT DOCUMENTS

| | | | |
|---|---|---|---|
| 3,675,210 A | * | 7/1972 | Block et al. ................... 702/66 |
| 4,100,416 A | | 7/1978 | Hirschfeld |
| 4,300,834 A | | 11/1981 | Demers et al. |
| 4,343,991 A | * | 8/1982 | Fujiwara et al. ....... 250/227.11 |
| 4,675,300 A | | 6/1987 | Zare et al. |
| 5,043,585 A | | 8/1991 | Fehrenbach et al. |
| 5,062,942 A | | 11/1991 | Kambara et al. |
| 5,066,382 A | | 11/1991 | Weinberger et al. |
| 5,198,091 A | | 3/1993 | Burolla et al. |
| 5,324,401 A | | 6/1994 | Yeung et al. ............... 204/452 |
| 5,338,427 A | | 8/1994 | Shartle et al. |
| 5,366,608 A | | 11/1994 | Kambara |
| 5,413,686 A | | 5/1995 | Klein et al. |
| 5,416,879 A | | 5/1995 | Liu |

(List continued on next page.)

FOREIGN PATENT DOCUMENTS

| | | | |
|---|---|---|---|
| WO | WO98/10122 | 3/1998 | ............ G25B/9/00 |
| WO | WO00/06996 | 2/2000 | .......... G01N/21/64 |
| WO | WO01/02846 | 1/2001 | ......... G01N/27/447 |

OTHER PUBLICATIONS

Taylor et al, Axial–Beam Laser–Excited Fluorescence Detection in Capillary Electrophoresis, Anal. Chem. 1992, vol. 64, 1741–1744.

Taylor et al, Multiplexed Fluorescence Detector for Capillary Electrophoresis Using Axial Optical Fiber Illumination, Anal. Chem. 1993, vol. 65, 956–960.

International Search Report of Counterpart PCT Application No. PCT/US02/02515.

*Primary Examiner*—Christopher W. Fulton
*Assistant Examiner*—R. Alexander Smith
(74) *Attorney, Agent, or Firm*—Liu & Liu (57) ABSTRACT

A multi-channel bio-separation detection method and apparatus in which a single detector is coupled to a plurality of radiation sources, in a one detector/many radiation sources configuration. Each radiation source directs radiation at one detection zone of a single separation channel, and a single detector is applied to detect light emissions from the detection zones of several separation channels. The light sources direct radiation at the detection zones in a predetermined sequence and further in a cyclic manner, with the detector output synchronized to the light sources by a controller. Bio-separation may be conducted simultaneously in all the channels in parallel, with detection time-staggered and/or time multiplexed with respect to the light sources. In one embodiment, low cost light emitting diodes may be used as light sources. In another aspect, the detection scheme is configured for radiation induced fluorescence detection in a multi-channel capillary electrophoresis instrument.

10 Claims, 5 Drawing Sheets

U.S. PATENT DOCUMENTS

| | | |
|---|---|---|
| 5,439,578 A | 8/1995 | Dovichi et al. |
| 5,498,324 A | 3/1996 | Yeung et al. ................ 204/452 |
| 5,529,679 A | 6/1996 | Takahashi et al. |
| 5,539,201 A | 7/1996 | Liva et al. |
| 5,543,018 A | 8/1996 | Stevens et al. |
| 5,560,811 A | 10/1996 | Briggs et al. |
| 5,584,982 A | 12/1996 | Dovichi et al. |
| 5,625,403 A | 4/1997 | Hazman et al. |
| 5,650,846 A | 7/1997 | Yin et al. |
| 5,675,155 A | 10/1997 | Pentoney, Jr. et al. ... 250/458.1 |
| 5,680,220 A | 10/1997 | Delignieres et al. |
| 5,736,410 A | 4/1998 | Zarling et al. |
| 5,741,411 A | 4/1998 | Yeung et al. |
| 5,741,412 A | 4/1998 | Dovichi et al. |
| 5,763,277 A | 6/1998 | Zhu et al. |
| 5,779,978 A | 7/1998 | Hartmann et al. |
| 5,784,157 A | 7/1998 | Gorfinkel et al. |
| 5,790,727 A | 8/1998 | Dhadwal et al. ............ 356/246 |
| 5,846,727 A | 12/1998 | Soper et al. |
| 5,865,974 A | 2/1999 | Cabilly et al. |
| 5,916,428 A | 6/1999 | Kane et al. |
| 5,968,331 A | 10/1999 | Kambara et al. |
| 5,999,250 A | 12/1999 | Hairston et al. |
| 6,001,230 A | 12/1999 | Burolla |
| 6,017,765 A | 1/2000 | Yamada et al. |
| 6,027,627 A | 2/2000 | Li et al. |
| 6,043,880 A | 3/2000 | Andrews et al. |
| 6,054,032 A | 4/2000 | Haddad et al. |
| 6,063,251 A | 5/2000 | Kane et al. |
| 6,074,827 A | 6/2000 | Nelson et al. |
| 6,084,667 A * | 7/2000 | Melman et al. ............. 356/246 |
| 6,103,083 A | 8/2000 | Merenkova et al. ........ 204/603 |
| 6,104,485 A | 8/2000 | Wang et al. |
| 6,132,578 A | 10/2000 | Kambara et al. |
| 6,153,437 A | 11/2000 | Horn |
| 6,184,990 B1 | 2/2001 | Amirkhanian et al. |
| 6,326,213 B1 | 12/2001 | Letcher et al. |
| 6,361,672 B1 * | 3/2002 | Zhu et al. ................... 204/603 |
| 6,369,893 B1 | 4/2002 | Christel et al. |
| 6,597,450 B1 * | 7/2003 | Andrews et al. ............ 356/317 |
| 6,759,662 B1 * | 7/2004 | Li ........................... 250/458.1 |

\* cited by examiner

OPTICAL DETECTION IN A MULTI-CHANNEL BIO-SEPARATION SYSTEM

This application claims the priority of U.S. Provisional Patent Application No. 60/264,553, filed Jan. 26, 2001.

CROSS-REFERENCE

U.S. patent application Ser. No. 10/059,993 entitled Multi-Channel Bio-Separation Cartridge, concurrently filed on Jan. 28, 2002, which is assigned to BioCal Technology, Inc., the assignee of the present invention, and which is fully incorporated by reference herein.

BACKGROUND OF THE INVENTION

1. Field of the Invention

The present invention relates to detection techniques in bio-analysis, particularly optical detection in a multi-channel bio-separation system, and more particularly detection of emissions from radiation excitations in multi-channel capillary based electrophoresis. The present invention further relates to bio-separation instrument incorporating the detection scheme of the present invention.

2. Description of Related Art

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to make easy sample handling during the process, and in general, to have a simplified, low cost, high sensitivity detector.

One type of DNA analysis instruments separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a multi-lane slab gel electrophoresis instrument, which as the name suggests, uses a slab of gel on which DNA samples are placed. Electric charges are applied across the gel slab, which cause the DNA sample to be separated into DNA fragments of different masses.

Another type of electrophoresis instruments is the capillary electrophoresis (CE) instrument. CE refers to a family of related analytical techniques that uses very strong electric fields to separate molecules within narrow-bore capillaries (typically 20–100 um internal diameter). CE techniques are employed in seemingly limitless applications in both industry and academia. Gel- and polymer network-based CE has revolutionized studies of nucleic acids; applications include DNA sequencing, nucleotide quantification, and mutation/polymorphism analysis. By applying electrophoresis in a fused silica capillary column carrying a buffer solution, the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample.

Some of the challenges in designing CE-based instruments and CE analysis protocols relates to sample detection techniques. In the case of fluorescence detection, considerable design considerations had been given to, for example, radiation source, optical detection, sensitivity and reliability of the detection, cost and reliability of the structure of the detection optics.

CE with the use of the fluorescence method provides high detection sensitivity for DNA analysis. Fluorescence detection is often the detection method of choice in the fields of genomics and proteomics because of its outstanding sensitivity compared to other detection methods. Two prevailing fluorescence detection modes are confocal scanning laser induced fluorescence (LIF) and sheath flow detectors.

The main drawback of the sheath flow detector is the highly sophisticated flow system needed to ensure a reliable sheath flow. Extreme demands are put on the optical and mechanical component tolerances in order to meet the robustness demands of end-users. The sensitivity of the device is very good, but it is not obvious that this principle of fluorescence detection is suited for a high-throughput yet low cost DNA analysis. The scanning confocal detector is based on scanning the optical system. The use of moving parts is not ideal when considering simplicity, robustness and lower cost of the instrument. Also, the shallow focal depth of the microscope objective puts severe demands on the mechanical and optical component tolerances. Further, the optical scanning principle reduces the duty cycle per capillary, which may impair the sensitivity when scaling up the instrument further for very high-throughput purposes.

One of the most expensive hardware components for many commercially available CE instruments with LIF detector is typically a fluorescence excitation light source, which can be a gas discharge lamp (mercury or xenon) or a laser (gas, solid state with second harmonic generation, dye, or semiconductor), that are bulky, expensive, inefficient and difficult to couple one's light output into optical fibers, thus preventing miniaturization of the optical detection system. These light sources hinder development of small size, high-throughput and cost-effective analytical instruments, with the convenience required for rapid detection.

Separation of DNA fragments by size using gel-filled capillaries has advantages over the classical slab gel-based separations in terms of speed and resolution. However, most commercially available CE instrumentation has only one capillary, and only one sample may be analyzed at a time. In a commercial automated DNA sequencer utilizing a slab gel system (such as the Applied BioSystems 377 instrument), 36 samples may be analyzed simultaneously. In order for capillary electrophoreis based DNA fragment analyzing instrumentation to be competitive on a throughput basis, it has been necessary to develop instruments that can run more than one sample at a time. The principle involved in DNA fragment Analyzing instruments (such as PACE 5000 LIF, PACE MDQ LIF of Beckman Coulter) using a single-capillary instrument can be extended to multi-capillary system. However, the design of a multi-capillary DNA Analyzer utilizing LIF based detection optical systems (i.e. 8-capillary CEQ™ 2000XL Instrument of Beckman Coulter) are considerably more costly and complicated than the classical slab gel-based systems. Other examples of commercially available multi-capillary CE instruments include instruments developed by ABI, SpectruMedix and Pharmecia, which shared similar drawbacks.

Another fluorescence detection method illuminates the interiors of multiple capillaries simultaneously, and collects the light emitted from them. As in U.S. Pat. No. 5,790,727, the capillaries in a parallel array form an optical wave guide wherein refraction at the cylindrical surfaces confines illuminating light directed in the plane of the array to the core of each adjacent capillary in the array. However, because only one light source is used for the illumination, there is cross talk between the different separation channels defined by the capillaries. Due to the existence of scatter light, cross talk cannot be prevented and the contrast ratio of detected signals will be poor due to noise in the fluorescence emission. Furthermore, prior art single illumination source for multiple channels makes multi-wavelength LIF detection more complicated.

It is therefore desirable to develop a low-cost high throughput multi-channel detection scheme for bio-separation, which would overcome the limitations in the prior art.

SUMMARY OF THE INVENTION

The present invention provides a simplified, low cost, efficient, highly sensitive, and high throughput multi-channel detection configuration for bio-separation (e.g., CE), which overcomes the drawback of the prior art. The present invention provides a multi-channel detection scheme based on a multi-radiation source/common detector configuration, in which detection is conducted in a time-staggered, and/or time-multiplexed detection for the channels. A single detector is coupled to a plurality of radiation sources, in a one detector/many radiation sources configuration. Each radiation source directs radiation at one detection zone of a single separation channel, and a single detector is applied to detect light emissions from the detection zones of several separation channels. There may be more than one detector in the entire detection system, each serving multiple radiation sources.

Bio-separation may be conducted simultaneously in all the channels in parallel, with detection time-staggered and/or time-multiplexed with respect to the light sources. The light sources direct radiation at the detection zones in a predetermined sequence in a cyclic manner, with the detector output synchronized to the light sources by a controller. The radiation sources and the detector are pulsed in synchronization in a time-multiplexed manner. The controller controls the detector and radiation sources in a manner to effect detection of radiation emissions from the multiple separation channels in predetermined detection cycles, wherein each detection cycle is repeated at a frequency to provide a desired detection time or duration. The controller controls the radiation sources and detector in a manner to effect detection in a repeated scanning manner, across the detection zones of the separation channels, in a time-staggered type detection. In accordance with the present invention, cross talk between channels is virtually eliminated. No moving parts are required for directing the light source or detection.

In one embodiment, low cost light emitting diodes (LEDs) (e.g., super bright LEDs) or laser diodes, instead of expensive high power lasers may be used as light sources. Alternatively, low energy lasers may be used. The incident light from the light sources may be separately directed to the detection multi-channel detection zones using optic fibers. The emitted light from the multi-channel detection zones may be directed to one or more common detectors using optic fibers. Since no moving parts are necessary, component count can be reduced. By eliminating or reducing cross talk between channels, the optical detection system design can be much simplified. Accordingly, the cost, reliability, and ease of use of the instrument is improved.

In a particular embodiment of the present invention, the detection scheme of the present invention is configured for radiation induced fluorescence detection in a multi-channel bio-separation instrument. In another embodiment, the detection scheme is configured for radiation induced fluorescence detection in a capillary electrophoresis instrument.

In another aspect of the present invention, the present invention provides a bio-separation instrument that incorporates the detection scheme of the present invention.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF THE ILLUSTRATED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed to a novel detection configuration in which multiple light sources emit excitation light through respective optical fiber toward respective fluid sample in a plurality of fluid samples in a time-multiplexed manner; fluorescence is generated in each of the fluid samples in response to the excitation light at different times corresponding to the times at which the light is transmitted to the samples; and the fluorescence from a single sample is delivered to the detector, which outputs a signal proportional to the intensity of the detected fluorescent light. Therefore, a single detector is used to detect light from a plurality of light emitting devices. For purpose of illustrating the principles of the present invention and not limitation, the present invention is described by reference to embodiments directed to CE, radiation induced fluorescence, and multiple separation channels. It is understood that the scope of the present invention is not limited to detection of fluorescence type of emission, but is also applicable to detection of other types of emissive radiation, such as phosphorescence, luminescence and chemiluminescence.

Figure 1:
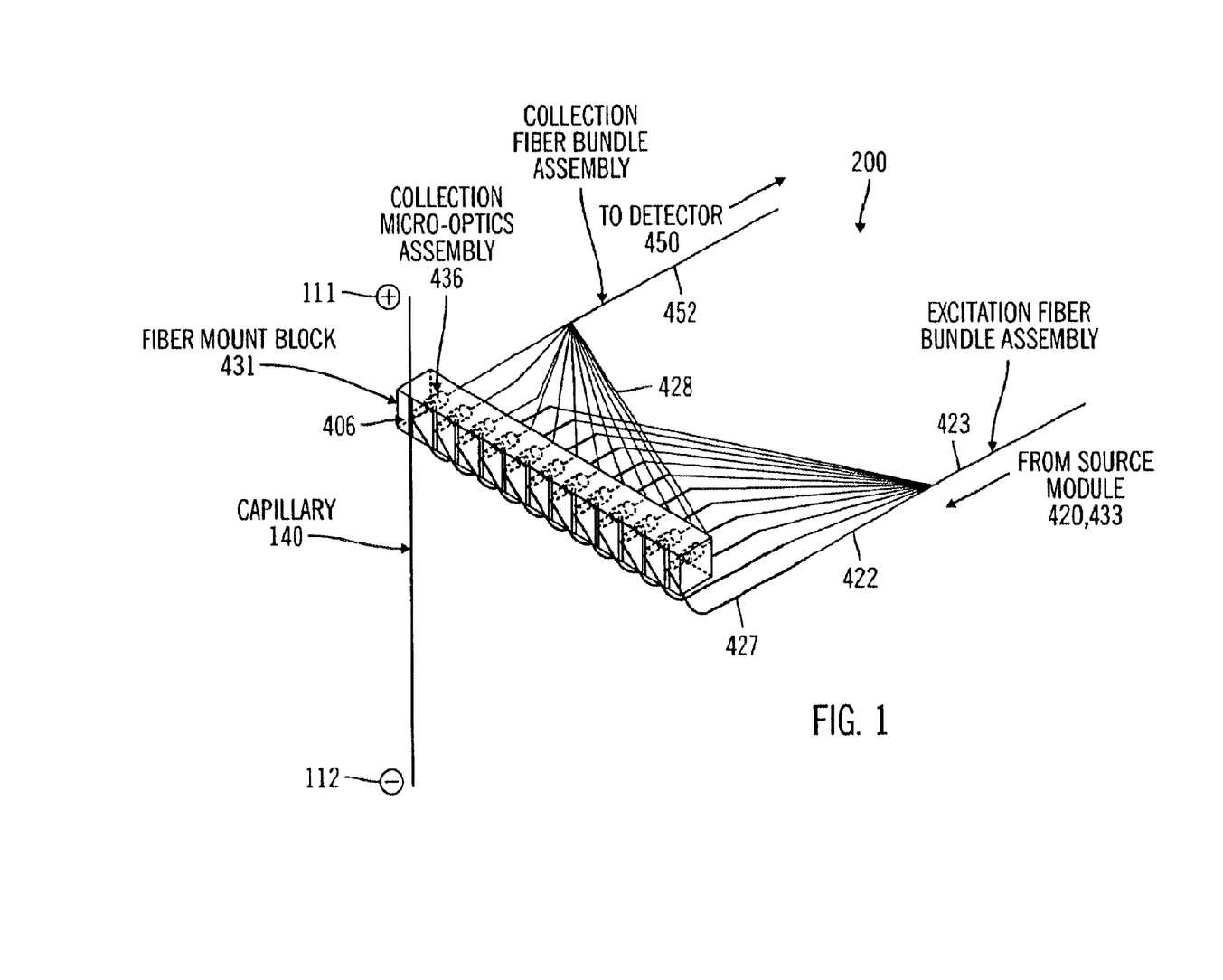
FIG. 1 is a schematic view of an example of a multi-channel bio-separation system that incorporates the optical detection concept of the present invention.

The mechanism of electrophoresis and radiation induced fluorescence when considered alone are outside the scope of the present invention. For the sake of completeness, it is sufficient to briefly describe CE in reference to the multi-channel CE system 200 in reference to FIG. 1 and FIG. 2. As shown in FIG. 1, the CE system 200 generally comprises at least one capillary separation column 140, having a separation channel and a detection section defining a detection zone 406. The separation channel is filled with a separation support medium, which may be simply a running buffer, or a sieving gel matrix known in the art. For radiation induced fluorescence detection, the gel matrix includes a known fluorophore, such as Ethidium Bromide.

In operation, a prepared biological sample (e.g., a DNA sample) is introduced into the far end of the capillary column 140 away from the detection zone 406, by any of a number of ways that is not part of the present invention (e.g., electrokinetic injection from a sample reservoir or physical pressure injection using a syringe pump). The sample binds to the fluorophore. When a DC potential is applied between electrodes 111 and 112, the sample migrates under the applied electric potential along the separation channel and separates into bands of sample components. The extent of separation and distance moved along the separation channel depends on a number of factors, such as migration mobility of the sample components, the mass and size or length of the sample components, and the separation support medium. The driving forces in the separation channel for the separation of samples could be electrophoretic, pressure, or electroosmotic flow (EOF) means.

When the sample reaches the detection zone 406, excitation radiation is directed from light source 420 via the excitation fiber 422 at the detection zone. The sample components would fluoresce with intensities proportional to the concentrations of the respective sample components (proportional to the amount of fluorescent tag material). The detection fiber 428 collects the emitted fluorescence, at a wavelength different from that of the incident radiation and direct to a detector 450.

Figure 2:
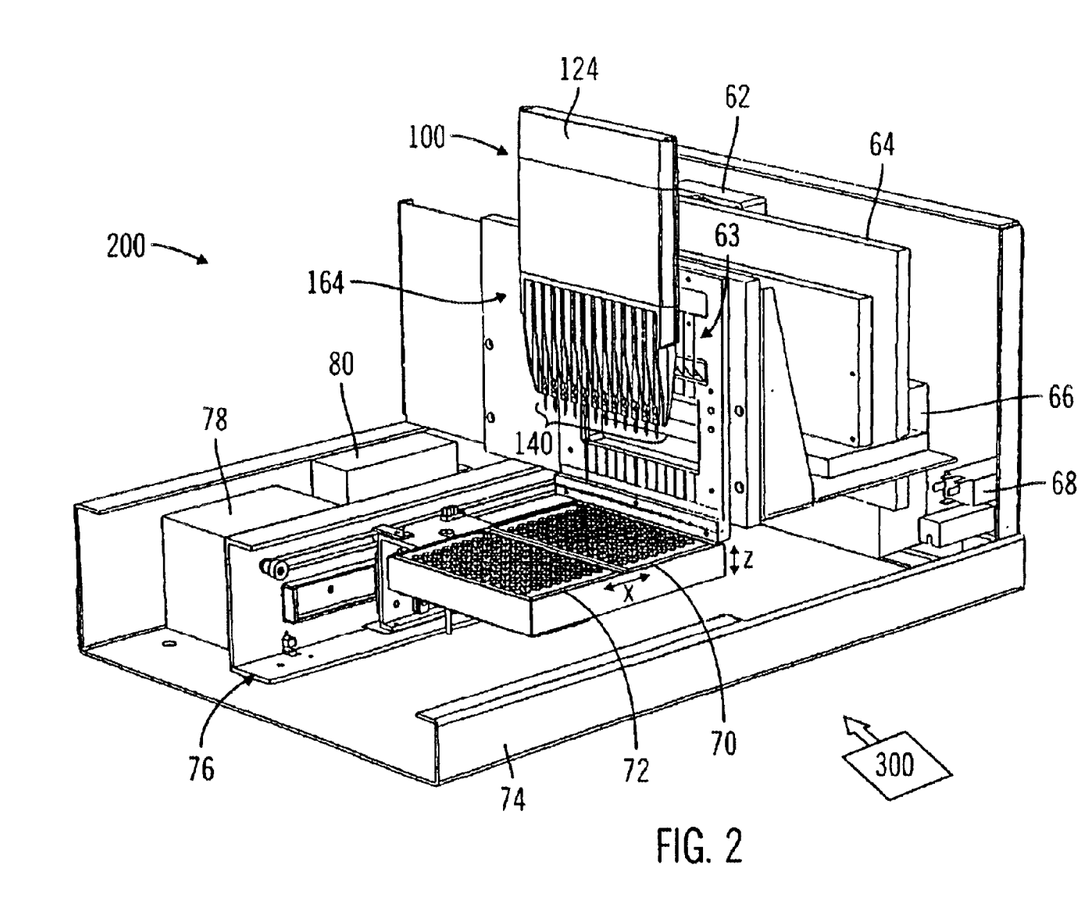
FIG. 2 is a perspective view of a multi-channel CE system, which incorporates the optical detection scheme of the present invention, in accordance with one embodiment of the present invention.

In one embodiment of the invention, referring to FIG. 2, a multi-channel cartridge 100 and CE system 200 that is adapted for use with the present invention is schematically illustrated. (U.S. patent application Ser. No. 10/059,993 entitled Multi-Channel Bio-Separation Cartridge, concurrently filed on Jan. 28, 2002, which is assigned to BioCal Technology, Inc., the assignee of the present invention, and which has been fully incorporated by reference herein, is more specifically directed to various embodiments of the gel filled multiple capillary cartridge and the CE instrument in which the cartridge is designed to be used.) The fully automated DNA analysis instrument 200 has a base 74, supporting a modular X-Z sample handling tray mechanism 76, which moves two 96-well micro-titer plates 70 and 72 in relation to the multi-capillary cartridge 100 supported on support bracket 164. The system 200 provides easy handling of multi-channel separation columns, and allows easy optical coupling of the detection zones to the detection optics of the CE instrument 200.

The cartridge 100 includes a twelve-channel fused silica capillary array that is used for separation and detection of the samples as part of a disposable and/or portable, interchangeable cartridge assembly 100. The multi-channel capillary array includes twelve detection zones defined by microchannels in the cartridge 100. The multi-channel cartridge 100 shown in FIG. 2 holds up to 12 capillaries 140, 12–16 cm long. The multi-channel cartridge 100 is integrated with a top, outlet buffer reservoir 124 common to all capillaries 140, which is directly coupled to a modular air pressure pump 78. The pressure pump 78 provides the required air pressure to fill-up all the 12-capillaries with the sieving gel contained in the reservoir 124. Depending on the viscosity of the gel, pressures of up to 40 PSI may be applied to the capillaries 140 through the gel-filled reservoir 124. The cartridge gel-reservoir 124 is equipped with built in common electrode (anode; not shown) for all 12-capillaries, which is automatically connected to a high voltage power supply 80 for electrophoresis when installed inside the instrument 200. A fan or Peltier cooler 63 on the support bracket 164 adjacent to the cartridge 100 provides temperature control of the cartridge. Injection of the samples is achieved by electrokinetic methods. The high voltage power supply 80 is used to deliver 0-to-20 KV of electrical field to the gel-filled capillaries for the electrokinetic injection and separations of DNA fragments. Each of the 12-LED's broad band light energy (FWHM=47 nm) is relayed by individual light transmitting optical fibers (multi-mode silica or plastic 200 micron Core fibers, 0.22 N.A.) to each of the capillary's detection zone inside the cartridge 100 for the excitation of the separated DNA fragments. A power supply 66 provides DC power to the CE system 200. Additional details of the cartridge 100 and CE system 200 may be referenced in the copending patent application that has been incorporated by reference herein.

Figure 3:
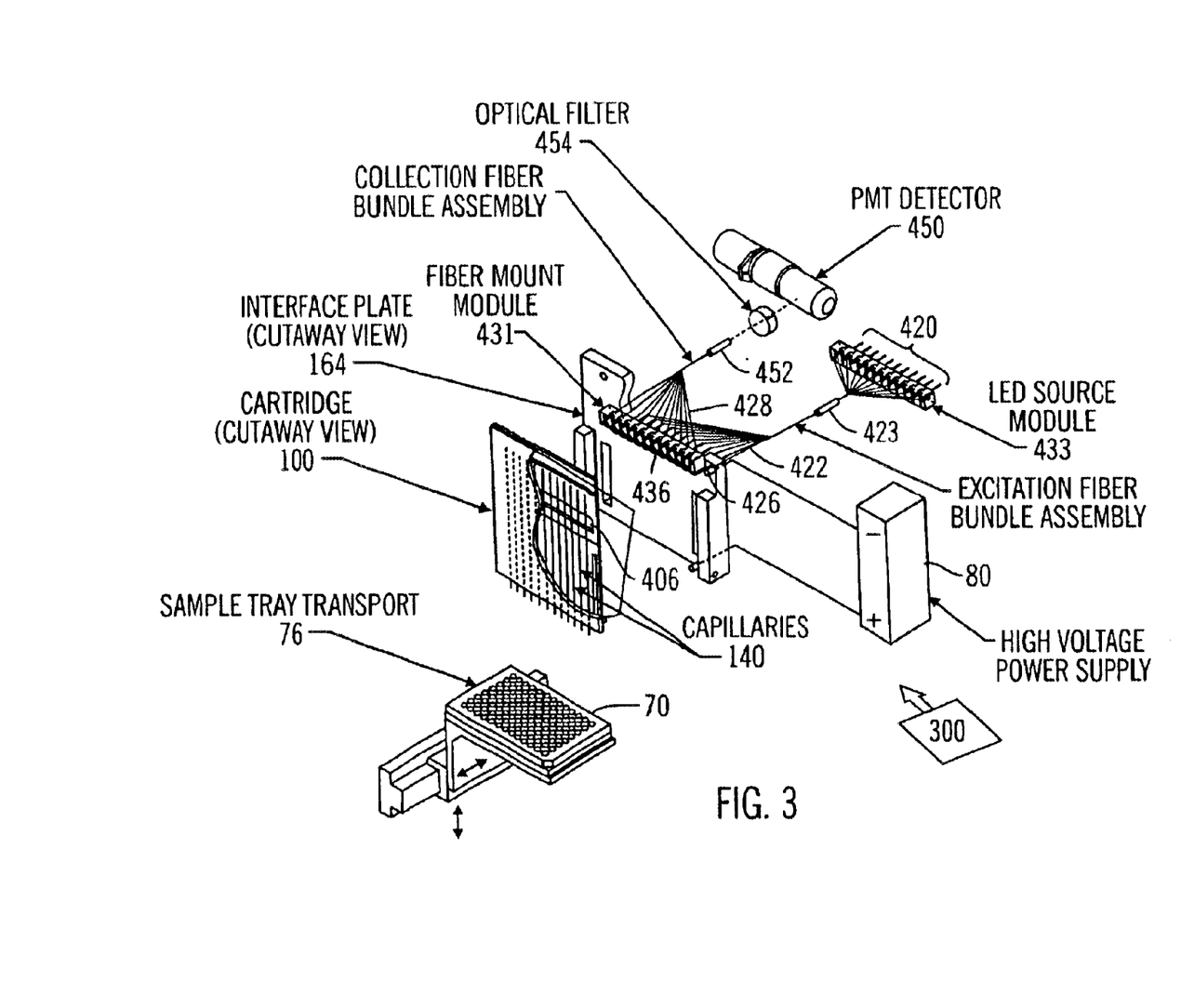
FIG. 3 is a simplified view of the detection optics in relation to the capillary cartridge in accordance with one embodiment of the present invention.

FIG. 3 schematically represents the detection optics and relationship to the cartridge 100, when the cartridge 100 (shown in simplified view) is attached to the CE system 200 in which it is designed for use, excitation fibers 422 (i.e., multi-mode silica or plastic fibers, 0.22 N.A.) in the systems are directed at the detection zone 406 of the capillaries 140. Each channel is separately coupled to an LED 420.

During electrophoresis, the rate at which the separated components or analytes move through the sieving gel is inversely proportional to their mass. As the fragments approach the detection zone 406, the excitation light energy from each of the twelve LEDs 420 supported in a LED module 433 is delivered by individual light transmitting optical fibers 422 (e.g., grouped in a bundle 423) to illuminate the separated components or analytes at the detection zone 406. The excitation light is delivered to the corresponding 12-capillaries directly with or without use of microlenses. The excitation fibers 422 may be coupled to each LED 420 by a micro-lens to improve optical coupling between the LEDs and the fibers. The fibers 422 are supported and aligned with respect to the capillary by a mount module or block 431. As the separated components or analytes move through the sieving gel (or linear polymer solution), an intercalating dye (Ethidium Bromide) within the sieving gel allows the separated components or analytes to be detected by detecting the light induced fluorescence.

The emitted fluorescent light from the capillary's detection zone 406 is then collected by several high N.A. (Numerical Aperture) micro-lenses 436 (e.g., High-index Sapphire Micro-lens) supported and aligned in the fiber mount block 431. The collected fluorescent light, which has a higher wavelength (large stoke shift) than the excitation light, is then routed by 12 larger core optical fibers 428 (370 $\mu$m OD, 0.22 NA fibers, but could also be in ranges of:

100–1000 μm OD, 0.12–0.5 NA) from each of the 12 capillary's detection zone 406 and is brought into a single detector 450 (R5984 Hamamatsu photomultiplier tube) as a single bifurcated bundle assembly 452. A single, e.g., 570–630 nm long pass optical filter 454 (OG-590) is used prior to detection to filter the emission signal from the output of the fiber bundle (each fiber) assembly 428.

The LEDs 420 are operated to emit light at different times (i.e., modulated). Hence, light from only one LED 420 from LED module 433 is delivered to single capillary 140 at any given time and is detected by the detector 450, which outputs a signal proportional to the intensity of the detected fluorescent emission. Light induced fluorescence detection is proceeded in a predetermine sequence and in a cyclic fashion for all the detection zones 406 at capillaries 140, in synchronization with the activations of the LEDs 420. Therefore, a single detector 450 is used to detect fluorescence emissions from a plurality of radiation emitting devices.

The twelve LEDs 420 are pulsed/modulated in a time-multiplexed manner with respect to the detector. The LEDs are pulsed, and similarly the detector is pulsed also. The detector just reads one LED or one channel at a time in a time-staggered manner. As the LEDs are pulsed and continuously exciting the fluorophor which is tagged with the separated DNA fragments through all channels running in parallel, the detector is also sampling or reading one channel at a time in a time-staggered manner. In essence, detection is conducted in a repeated scanning manner, across the detection zones of the array of capillaries 140. Twelve emission signals will reach the single PMT 450 in a time-staggered manner by a single fiber-bundle assembly or they could be individual emission collection fibers which are all combined to a single detector. These detection fibers do not need to be in a 1×12 fiber bundle assembly form. They could be 12 individual fibers which are mounted individually to a single detector module by a single mechanical block, so they could either be packaged either in a 12 closed round packed or linear array packed form, delivering total of 12 emission signals from the cartridge to a single PMT. The light emitting diodes 420 are operated to emit light pulsed at several hundred hertz but separated from each other by a delay.

In general, pulsing of the LEDs are pulsed are conduct in the following sequence in accordance with one embodiment of the present invention. When LED one comes on then detector comes on or detects emission light for LED number one, then LED one becomes off for the next 11 times because there are a total of 12 channels. So the pulsing of the LEDs is tied to the detector which is done in a sample and hold scheme. The sampling frequency may be 100 Hz per channel so the total modulation frequency for all 12 channels is 1200 Hz, which is the frequency for the two consecutive channels, with a duty cycle of 1/12. This sampling frequency may be different as long as the time-multiplexing of LEDs and the time-staggered type detection scheme is preserved. The data collection processing rate in the software may be set at 10 Hz with an adjustable rise time (i.e. 0.1 sec–1 sec). (To have the similar sampling frequency, a sampling frequency of 10 Hz instead of 100 Hz may be used, but sampling frequency and data collection processing rate are independent from each other.) Then the LED would be on for about 10 msec and off for 100 msec at 1/12 duty cycle. (This duty cycle will change as the number of capillaries increases or decreases).

Figure 5:
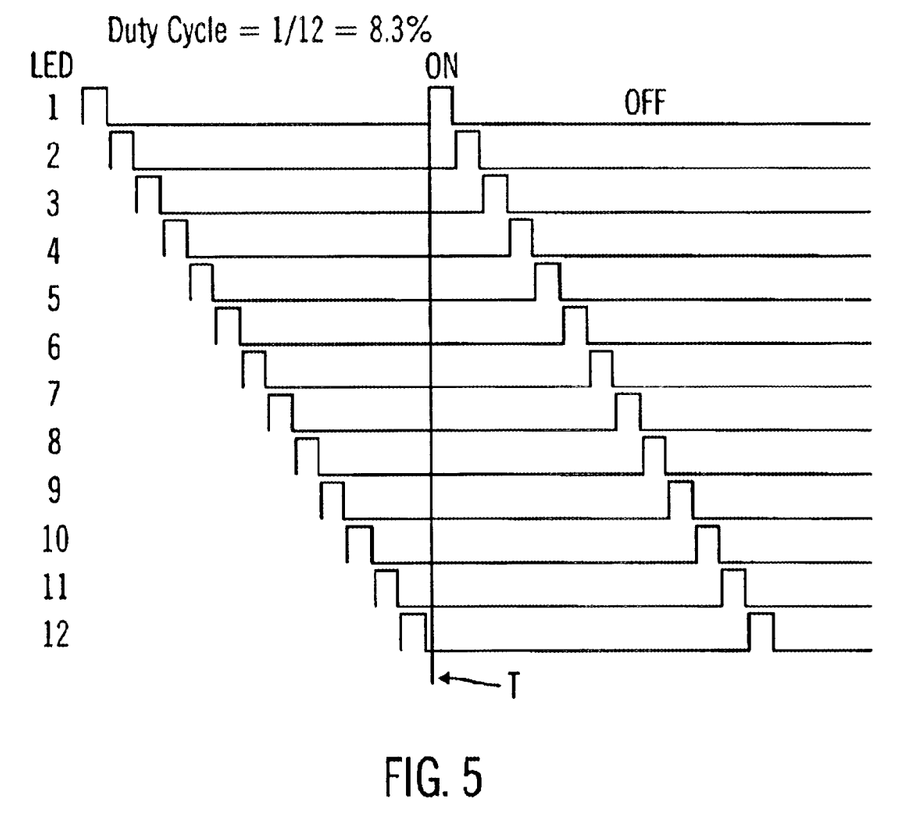
FIG. 5 is a timing diagram illustrating the pulsing for time-multiplexing of radiation sources in accordance with one embodiment of the present invention.

FIG. 5 shows the timing diagram of the pulsing of the LEDs, and similarly for the detector in accordance with one embodiment of the time staggered/time multiplexed detection scheme of the present invention. This is the timing diagram for the following example. The pulsing of LEDs is at 1/12 duty cycle. When a LED is on, it is on for 1/12 of the time (8.3%) and then is off for 11 times. The sampling frequency is 100 Hz/channel. 100 Hz is 10 msec. (T=1/f= 1/100 Hz=10 msec), which with a duty cycle of 1/12, then the LED is on for about 0.83 mSec or approximately 1 msec. All of the 12 LEDs are time-multiplexed in a time-staggered manner. So for a total of 12 channels, it is 1.2 KHz (1,200 Hz). The driving current for on time of LED is about 15–35 mA. The sampling frequency and the data collection processing rate in the software may be independent of each other.

As can be seen in FIG. 5, the pulsing train for time-multiplexing of LEDs proceed for one cycle up to time T, and then it repeats again. The same concept is applied for the detection side. The pulsing of the LEDs and the detector are synchronized. So as LED one comes on, the sample and hold for the produced (collected/detected) emission signals starts, and this is repeated for all 12-signals/LEDs, hence the time-staggered type detection. When the duty cycle is short, or the LED comes on for such a short period of time, it can produce high peak pulses in the detected signal. So LED off time is long during pulsing mode versus a constant on/DC operation, which means the LED can have longer life, because the cooling time (period) is long. One can take an advantage of this pulsing mode operation of LEDs and apply higher (as high as 100 mA) drive currents for generating higher intensities or peak powers. And one can also cool the LEDs to even drive them harder for higher peak powers. Accordingly, pulsing of LEDs help extend the life of the LEDs, and increase peak power/intensity.

It is noted that electrophoretic separations of fragments in the CE instrument 200 in accordance with the present invention are in seconds versus milliseconds for the pulsed LED on time. Because the pulsing frequency is much higher than the actual fragment peak separations, the time staggered/time multiplex detection scheme of the present invention does not negatively affect the sensitivity and performance of detection resolution. The resolution of the detection results (e.g., peaks in the detected signal) would depend in part on the gel matrix concentration, the separation inner diameter, length and the speed of migration through the detection zone 406. Experiments have shown that detection sensitivities of 100 ng/ml (0.02 ng of the DNA fragment) could be achieved with good resolution using the inventive detection scheme.

As an example, for a test sample comprising φX174 DNA fragment, with 75 μm by 16 cm capillary at 300 V/cm electrical potential, a baseline resolution for the 271/281 base pairs can be achieved. The STR loci in an individual DNA Identification type separations with standard markers show about a 4 base pair separation resolution using the a single color time-multiplexed fluorescence detection approach in accordance with one embodiment of the present invention. Separation time for all 12 channels running in parallel is less than 10 minutes with a good Signal-to-Noise ratio (S/N=150 for the largest fragment, based on peak-to-peak noise).

The pulsing of the radiation sources and the detection sampling rate and period should be synchronized so that the desired detection for a channel covers a period when only the associated radiation source is on with respect to the detector.

While the above described embodiment shows the source LEDs directing incident light to the capillaries via optic fibers 422, it is within the scope and spirit of the present invention to position the radiation sources, such as the LEDs, adjacent the detection zone 406, using short optic fiber alignment leads 427 to align incident light to the detection zone or completely eliminating use of fiber optics (e.g., by deploying micro-lenses to align incident light from LEDs directly to the capillary detection zone 406).

Figure 4:
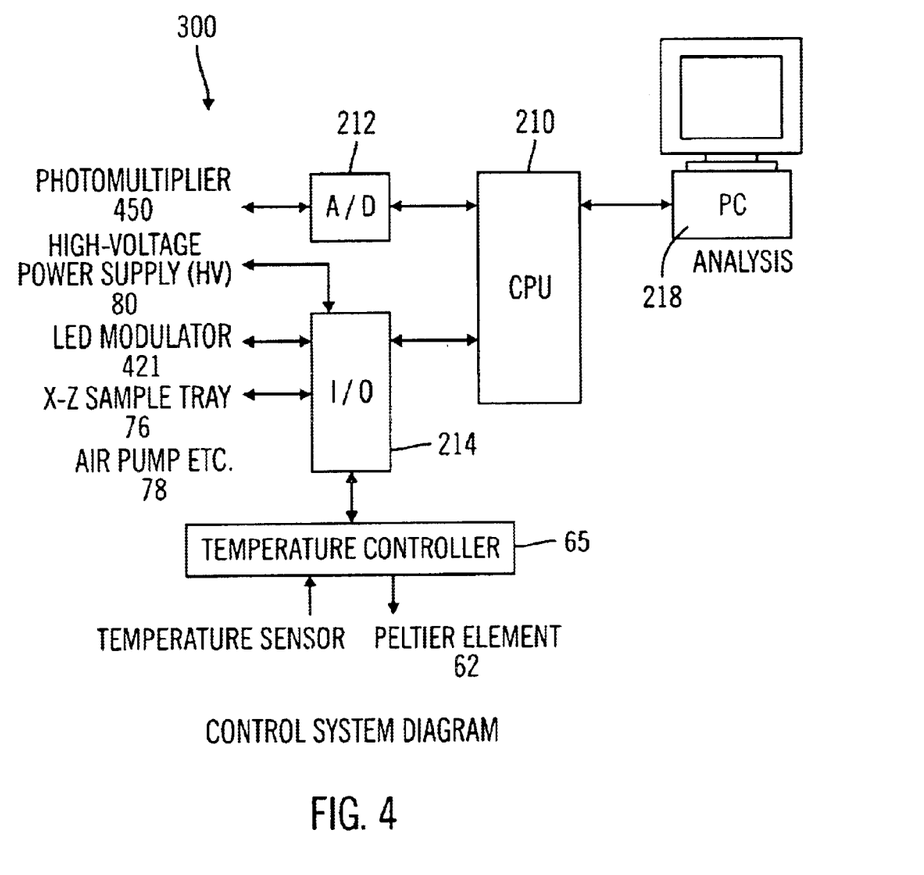
FIG. 4 is a block diagram of the control system for the incident radiation and emission detection system.

In a preferred embodiment, as shown in FIG. 4, there is shown a controller 300, which comprises a CPU 210, an A/D converter 212 for converting detection signals from the PMT 450 to corresponding digital signals, and an I/O interface 214 for transferring and receiving signals to and from respective parts of the CE instrument 200 by instructions from the CPU 210. A temperature controller 65 controls the fan or Peltier cooler 63 that controls the temperature of the electrophoresis chamber for the micro-channel/capillary array cartridge 100. The I/O interface 214 is coupled with the temperature controller 65, which also controls the high-voltage power supply for sample injection and electrophoresis functions of the CE instrument 200, a circuit 421 for modulating the LEDs 420, sensors, air pump, air valve, and motors for the X-Z stage of the CE instrument 200. The CPU 210 may be further coupled to an external personal computer 218, which in turn performs data processing or additional control function for the CE system 200. The CPU 210 and/or the PC 218 may be programmed with control functions dictated by LabVIEW™ software available from National Instruments Corporation, to control various features and functions of the automated multi-channel DNA analyzer 200.

The components of the controller 300, with the exception of the PC 218, may be packaged as an electronic board 64 (FIG. 2) and cooling fan 62, on board the CE system 200 and electrically coupled to the PC 218 via a serial port (not shown), or they may be part of a separate controller module outside of the CE system 200. The CPU 210 and/or the PC 218 are programmed to accomplish the various control functions and features for the CE system 200. In one embodiment, the PC 218 can be configured to provide the front panel control (i.e., user interface) for the instrument 200, and the board 64 may be configured to provided the time staggered/time multiplex detection controls. It would be within a person skilled in the art to implement the program code given the functions and features disclosed herein. An A/C power filter/switch 68 (FIG. 2) is provided for the instrument 200.

Incident radiation for the detection may be directed at the detection zone and/or radiation emissions from the detection zone may be output axially along the separation medium (references are made to U.S. patent application Ser. No. 09/887,871 entitled Optical Detection in Bio-Separation Device Using Axial Radiation Input; U.S. patent application Ser. No. 09/887,953 entitled Optical Detection in Bio-Separation Device Using Axial Radiation Output, and U.S. patent application Ser. No. 09/887,872 entitled Optical Detection in Bio-Separation Device Using a Widened Detection Zone, all filed on Jun. 22, 2001, which are commonly assigned to BioCal Technology, Inc., the assignee of the present invention, and which are fully incorporated by reference herein.

The present invention utilizes low cost and miniature LEDs as excitation sources. Other non-coherent, broadband light sources could be used (i.e., xenon lamps, D2 lamps, mercury lamps, arc lamps). The emissions from the detection zone are collected by micro-optical lenses with fiber delivery systems either from outside or inside the detection collar.

Super-bright LEDs (i.e. Agilent's InGaN LEDs in colors of blue, green, etc . . . ) are candidates for inexpensive, compact, low-power light sources for use in the detection scheme of the present invention. These super-bright LEDs based on InGaN material technology (HLMP-CB15 and HLMP-CM15 from Agilent) have an average light output power of 2.5–3 mW. The spectral characteristics of these blue-green InGaN LEDs with their Peak Wavelengths of 470 and 530 nm and halfwidths (nm) of 30 to 50 nm are good candidates to be used for excitation of dyes (e.g. fluorescin, rhodamine, Etidium Bromide, thiazol orange), with excitation spectra in the range of 450 to 550 nm. Any solid state light source that can be pulsed could also be used with any dye or fluorophor for this type of time-multiplexed detection. Since the response time of these LEDs are very high (few hundred nanoseconds in frequency ranges of 1 Hz-to-100 MHz), they could be pulsed at greater forward currents (e.g., 15–30 mA, but could be up to 100 mA forward current in pulsed mode operation), to obtain high radiant peaks. Pulsed operation of LEDs can typically be achieved by the transistor drive circuits. Significantly higher peak LED light output can be realized from large drive current pulses at lower duty cycles than DC operation. Another example is LED-array module consisting of Green 524 mn LEDs, which can also be adopted as excitation light sources for the fluorescence detection of a low-cost CE instrument.

While in the embodiments described above, the multiple radiation sources are at the same wavelength, it is within the scope and spirit of the present invention to configure the multiple radiation sources at different wavelengths, to complement the specific samples, sample based detection applications or gel chemistries in the different capillaries. For example, adjacent radiation sources may have alternating wavelengths, to run separations with identical samples in two adjacent capillaries with different gel chemistries and/or fluorescence tags, to allow comparison of the detection results for determining different or additional separated components in the sample, or as a basis of validation of the detection results. As another example, adjacent group of four capillaries may be incident with radiations of four different wavelengths (thus in the 12-channel system described above, there would be three groups of four channels) for the same sample. The same may be applied for detection of emissions from the channels incident with radiation of the same wavelength, in a time staggered and/or time multiplexed manner described above. Alternatively, there are multiple detectors, of same or different performance and/or detection characteristics, each applied for detection of emissions from the channels incident with radiations at the same wavelength in a time staggered and/or time multiplexed manner described above. Other variations are within the scope and spirit of the present invention.

The present invention may be extended to a system in which there are multiple wavelength excitation and detection for a single channel. Multiple radiation sources at various wavelengths may be applied to a single separation channel in a multi-channel system, and one or more detectors, at same or different detection characteristics, may be applied to detect the radiation emissions at same or different wavelengths from the channels, in a time staggered and/or time multiplexed manner similar to the method described above for a single wavelength excitation radiation. Reference to multiple wavelength excitation and detection is also made to U.S. Provisional Application No. 60/348,034 entitled "A Portable Multi-color Multiplexed Analysis Electrophoretic Device," filed on Oct. 19, 2001 which is commonly assigned to BioCal Technology, Inc., the assignee of the present invention, and which is fully incorporated by reference herein.

The innovative detection approach has many advantages over the existing commercial CE instruments. The detection system utilizes inexpensive light emitting diodes (LEDs) as excitation light sources for fluorescence type detection. The attractive features of LEDs as light sources are their low cost, small size, long lifetimes, good intensity stability resulting in low noise, and the possibility of direct electronic modulation. These smaller solid-state excitation light sources facilitate the fiber coupling, which results in miniaturization of the detection optics. Using a time-staggered detection approach by multiplexing of multi-LEDs provides a great advantage of reducing number of detectors (e.g., PMTs) to possibly one for multi-channel detection. By reduced component count and by simplifying the optical detection system design the cost, reliability and ease of use of the instrument is improved. There are negligible or no cross talks between separation channels.

While the invention has been particularly shown and described with reference to the preferred embodiments, it will be understood by those skilled in the art that various changes in form and detail may be made without departing from the spirit, scope, and teaching of the invention. For example, the excitation radiation source could be, for example, LEDs, laser diodes (semiconductor solid-state lasers), pulsed lasers (e.g., solid state lasers, gas lasers, dye lasers, fiber lasers), or other sources of radiation. LEDs (e.g., Green, 524 nm) are associated with low cost, super brightness, and small package. Alternate relative inexpensive light source for the present invention could be laser diodes in the visible, UV and/or infrared range. For example, laser diodes in the range of 400–900 nm, and more specifically in the range of 400–600 nm may be used, for example.

A person skilled in the art will recognize that the instrument incorporating the essence of this invention can also be used for biomoleculer analysis other than DNA analysis. For example, by altering the separation gel or buffer, the system can also be modified to analyze biomolecules like proteins, carbohydrates, and lipids.

By way of example and not limitation, the detection scheme of the present invention is described in connection with CE and radiation induced fluorescence detection. It is understood that the present invention is also applicable to detection of analytes separated based on bio-separation phenomenon other than electrophoresis, and detection of radiation emissions other than fluorescence emissions. Accordingly, the disclosed invention is to be considered merely as illustrative and limited in scope only as specified in the appended claims.

We claim:

1. A detection system for a bio-separation device having a plurality of separation channels in which bio-separation takes place simultaneously, comprising:
   a detection section along each separation channel defining a detection zone for analytes;
   a plurality of radiation sources, each comprising an LED associated with one of said separation channels;
   excitation means for introducing excitation radiation from the radiation sources at the detection zones as analytes pass the detection zones;
   detecting means for detecting radiation emissions from the detection zones, said detection means comprising a single detector associated with said plurality of radiation sources;
   control means for controlling the radiation sources and detecting means in a manner such that excitation radiation is introduced at the detection zone of each separation channel in a predetermined sequence and radiation emission from the detection zone of each separation channel is detected in a time staggered manner, wherein the control means controls the plurality of radiation sources to activate in successive pulses with respect to the radiation sources, and wherein the control means controls the synchronization of pulses of the radiation sources and detection sampling rate and period by taking into account the lag time in emitted radiation in adjacent separation channels, whereby desired detection for one of said separation channels covers a period when only the associated radiation source is on with respect to the detecting means.

2. The detection system as in claim 1, wherein the control means controls the detecting means to sample the radiation emissions from the multiple separation channels at a rate and period that provide desired radiation emission signal separation between the separation channels to reduce cross talk.

3. The detection system as in claim 1, wherein the control means controls the detecting means and radiation sources in a manner to effect the detection of radiation emissions from the multiple separation channels in predetermined detection cycles, wherein each detection cycle is repeated at a frequency to provide a desired detection resolution.

4. The detection system as in claim 1, wherein the control means controls the radiation sources and detecting means in a manner to effect detection in a repeated scanning manner, across the detection zones of the separation channels.

5. The detection system as in claim 1, wherein the radiation sources produces said excitation radiation at more than one wavelength.

6. The detection system as in claim 1 wherein the analytes comprise a material that fluoresces in the presence of the excitation radiation, and the detecting means comprises means for detecting fluorescence emission of the material.

7. The detection system as in claim 1 wherein the radiation emission is at least one of:
   fluorescene;
   chemiluminescence; and
   phosphorescence.

8. A bio-separation instrument, comprising:
   a plurality of separation channels;
   means for simultaneously separating samples in the separation channels into analytes; and
   a detection system, comprising:
      a detection section along each separation channel defining a detection zone for analytes;
      a plurality of radiation sources, each comprising an LED associated with one of said separation channels;
      excitation means for introducing excitation radiation from the radiation sources at the detection zones as analytes pass the detection zones;
      detecting means for detecting radiation emissions from the detection zones, said detection means comprising a single detector associated with said plurality of radiation sources;
   control means for controlling the radiation sources and detecting means in a manner such that excitation radiation is introduced at the detection zone of each separation channel in a predetermined sequence and radiation emission from the detection zone of each separation channel is detected in a time staggered manner, wherein the control means controls the plurality of radiation sources to activate in successive pulses with respect to the radiation sources, and wherein the control means controls the synchronization of pulses of the radiation sources and detection sampling rate and period by taking into account the lag time in emitted radiation in adjacent separation channels, whereby desired detection for one of said separation channels covers a period when only the associated radiation source is on with respect to the detecting means.

9. A bio-separation instrument as in claim 8, wherein the separation channel is defined by a capillary column, and the means for separating a sample is configured to effect separation of the sample by electrophoresis.

10. A method for detecting analytes in a bio-separation device having a plurality of separation channels in which bio-separation takes place simultaneously, comprising the steps of:

defining a detection zone for analytes along each separation channels;

providing a plurality of radiation sources, each comprising an LED associated with one of said separation channels;

introducing excitation radiation from the radiation sources at the detection zones as analytes pass the detection zones;

providing a single detector for detecting radiation emissions from the detection zones, wherein said single detector is associated with said plurality of radiation sources;

controlling the radiation sources and detector in a manner such that excitation radiation is introduced at the detection zone of each separation channel in a predetermined sequence and radiation emission from the detection zone of each separation channel is detected in a time staggered manner, wherein the control means controls the plurality of radiation sources to activate in successive pulses with respect to the radiation sources, and wherein the control means controls the synchronization of pulses of the radiation sources and detection sampling rate and period by taking into account the lag time in emitted radiation in adjacent separation channels, whereby desired detection for one of said separation channels covers a period when only the associated radiation source is on with respect to the detector.

* * * * *